US009826742B2

(12) United States Patent
Belkind et al.

(10) Patent No.: US 9,826,742 B2
(45) Date of Patent: *Nov. 28, 2017

(54) OCTANOIC, NONANOIC AND DECANOIC FATTY ACIDS WITH A PYRETHROID ADULTICIDE

(71) Applicant: Valent BioSciences Corporation, Libertyville, IL (US)

(72) Inventors: Benjamin A. Belkind, Wilmette, IL (US); Jason Clark, Elkhorn, WI (US); Peter DeChant, Portland, OR (US)

(73) Assignee: VALENT BIOSCIENCES CORPORATION, Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/346,172

(22) Filed: Nov. 8, 2016

(65) Prior Publication Data
US 2017/0049108 A1    Feb. 23, 2017

Related U.S. Application Data

(63) Continuation-in-part of application No. 14/504,921, filed on Oct. 2, 2014, now Pat. No. 9,572,346.

(60) Provisional application No. 61/885,754, filed on Oct. 2, 2013.

(51) Int. Cl.
*A01N 53/00*    (2006.01)
*A01N 25/08*    (2006.01)
*A01N 37/02*    (2006.01)

(52) U.S. Cl.
CPC ............. *A01N 53/00* (2013.01); *A01N 25/08* (2013.01); *A01N 37/02* (2013.01)

(58) Field of Classification Search
None
See application file for complete search history.

(56) References Cited

U.S. PATENT DOCUMENTS

| 5,334,585 | A  | 8/1994  | Derian et al. |
| 6,306,415 | B1 | 10/2001 | Reifenrath |
| 6,444,216 | B2 | 9/2002  | Reifenrath |
| 8,911,757 | B2 | 12/2014 | Reifenrath |
| 2012/0136056 | A1 | 5/2012 | Reifenrath |

OTHER PUBLICATIONS

International Search Report and Written Opinion issued by the International Bureau on Dec. 31, 2014.
McAllister, et al.,"Mode of Action for Natural Products Isolated from Essential Oils of Two Trees is Different From Available Mosquito Adulticides", J. Med. Entomol. 47(6): 1123-1126, (2010).
U.S. Environmental Protection Agency, Emery Oleochemicals LLC; Emerion Label 8000 C8910 FA Blend, date of issuance Jan. 17, 2014.

*Primary Examiner* — Bethany Barham
*Assistant Examiner* — Barbara Frazier
(74) *Attorney, Agent, or Firm* — Wood, Phillips, Katz, Clark & Mortimer

(57) ABSTRACT

The invention relates to an octanoic, nonanoic and decanoic (C8, 9, 10) fatty acids mixture with a pyrethroid. The invention also relates to methods of using the octanoic, nonanoic and decanoic (C8, 9, 10) fatty acids and pyrethroid mixture to achieve superior arthropod control.

15 Claims, 3 Drawing Sheets

Time/Mortality Response of Susceptible and Resistant *Aedes aegypti* to a 1:0.01 ratio of C8910 with Permethrin in Bottle Bioassay Time/Mortality Response of Susceptible and Resistant *Aedes aegypti* to Permethrin in Bottle Bioassay Time/Mortality Response of Susceptible and Resistant *Aedes aegypti* to C8910 in Bottle Bioassay Time/Mortality Response of Susceptible and Resistant *Aedes aegypti* to a 1:0.01 ratio of C8910 with Permethrin in Bottle Bioassay

OCTANOIC, NONANOIC AND DECANOIC FATTY ACIDS WITH A PYRETHROID ADULTICIDE

FIELD OF THE INVENTION

The present invention is directed to a mixture of octanoic, nonanoic and decanoic fatty acids and a pyrethroid.

BACKGROUND OF THE INVENTION

Arthropods, such as mosquitoes, are often a nuisance to humans and other animals. Arthropods can also be vectors for diseases. Due to the nuisance and public health issues, humans strive to control arthropod populations near their environments. One way of controlling arthropods is by using pyrethroids.

Pyrethroids are axonic excitoxins which prevent the closure of the voltage-gated sodium channels in the axonal membranes of arthropods. The toxins work by paralyzing the organism.

While pyrethroids are effective arthropod adulticides, a major problem is that populations of arthropods are developing resistance to them. Pyrethroid resistance, caused either by specific detoxification enzymes or an altered target site mechanism (Jcdr-type mutations in the sodium channels), has been reported on most continents in the majority of medically important mosquito species. If resistance continues to develop and spread at the current rate, it may render such insecticides ineffective in their current form. Such a scenario would have potentially devastating consequences in public health terms, because there are as yet no obvious alternatives to many of the pyrethroids.

Resistance is a complex phenomenon arising from exposure to the same or a similar insecticide class over a period of multiple insect generations. Resistance develops due to extinction of susceptible individuals within the population and survival with subsequent reproduction of individuals who are inherently "immune" to the effects of the insecticide. Resistance can be due to multiple factors that include selection of target site mutations, detoxification enzymes and decreased cuticular penetration. Resistance may arise in naïve populations that have been previously identified as insecticide susceptible or those that have been exposed to insecticides of another or similar class or mode of action. Cross resistance can occur and, in addition to physiological resistance, behavioral resistance mechanisms may also be present. The end result of resistance to current control measures is that available insecticides are often inadequate to provide the mortality rates necessary achieve sufficient levels of arthropod control at environmentally acceptable application rates. Because pyrethroid resistant insects pose a significant human health risk, there is a need in the art for a safe and effective arthropod insecticide.

One type of arthropod that is a major health concern is mosquitoes. The three major genera of mosquitoes which transmit diseases are *Anopheles, Culex* and *Aedes*. Therefore, there is a need to control mosquitoes to reduce disease transmission.

Insecticides can attack any stage of the insects' development. However, it is the mosquito in the adult stage that transmits viruses and parasites which cause disease. Control of larval stages is a first line of defense for suppression of mosquito populations, but without the capacity to control adult mosquitoes the ability to manage disease can be severely compromised in many settings.

In the past, the problem of insecticide resistance has been solved by rotating conventional insecticides of varying chemistries. However, resistance to multiple chemistries has developed in many settings, complicating this approach. Therefore, there is a need for a new approach to overcoming insecticidal resistance.

U.S. Pat. No. 6,306,415 is directed to methods of repelling flies by topically applying a composition containing a 1:1:1 ratio of octanoic acid, nonanoic acid and decanoic acid as the only active ingredients. U.S. Pat. No. 6,444,216 is directed to compositions and methods to repel insects containing a mixture of fatty acids as the only active ingredients. These patents do not discuss the possibility of using these compounds in combination with a pyrethroid.

McAllister, et al., *Mode of Action for Natural Products Isolated from Essential Oils of Two Trees is Different From Available Mosquito Adulticides*, J. Med. Entomol. 47(6): 1123-1126, discusses the possible utility of thymoquinone, nootkatone, and carvacrol for treating pyrethroid resistant strains of mosquitoes, but does not discuss the possibility of using these compounds in combination with pyrethroids.

The compositions of the prior art have failed to produce an environmentally safe adulticide that is effective on pyrethroid resistant and pyrethroid susceptible arthropods.

SUMMARY OF THE INVENTION

In one aspect, the invention is directed to a pesticidal mixture comprising an effective amount of octanoic, nonanoic and decanoic (C8, 9, 10) fatty acids and an effective amount of a pyrethroid.

In another aspect, the invention is directed to a method of insect control comprising administering to an environment in need of insect control an effective amount of a mixture of the present invention.

DETAILED DESCRIPTION OF THE INVENTION

Figure 1:
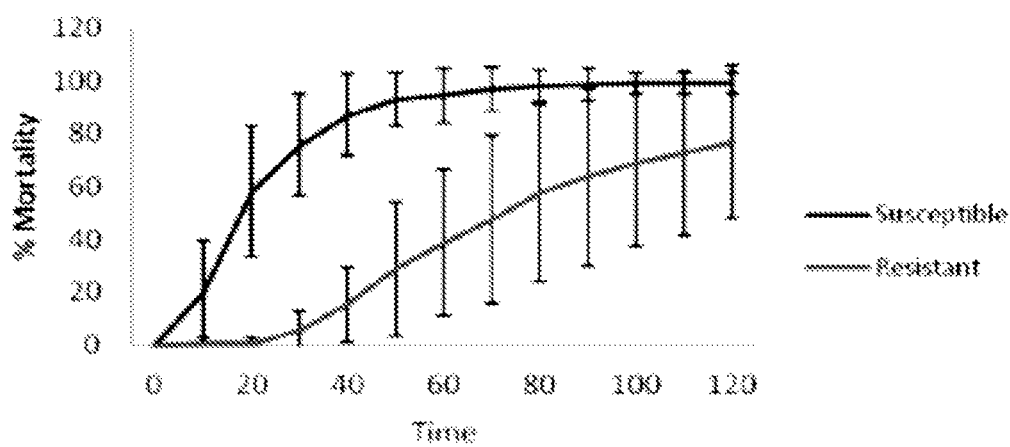
FIG. 1, Time/Mortality Response of Susceptible and Resistant *Aedes aegypti* to Permethrin in Bottle Bioassay, is a graph of the results from Bottle Bioassay Example #1. This bioassay confirmed that the *Aedes aegypti* strain was resistant to pyrethroids.

Applicants discovered that a mixture of octanoic, nonanoic and decanoic acids (C8, 9, 10) with a pyrethroid produces insecticidal compounds that are highly effective against adult mosquitoes. Additionally, the present mixture provides quick knockdown of insects, and a high mortality rate.

Unexpectedly, the mixture of octanoic, nonanoic and decanoic fatty acids (C8, 9, 10) with a pyrethroid provides superior control of pyrethroid resistant mosquitos. This was unexpected because one of skill in the art would not have expected mosquitos that have developed a resistance to pyrethroids to be killed by pyrethroid exposure when octanoic, nonanoic and decanoic fatty acids are present. U.S. Pat. Nos. 6,306,415 and 6,444,216, as explained above, refer to repelling insects with fatty acids but fail to suggest increased mortality rates. Accordingly, it would not be expected that an insect would be killed by a combination of a compound that it has already become resistant to and a repellant.

In addition, the mixtures of the present invention provide higher kill rates than pyrethroids alone on pyrethroid susceptible species. It was not expected that the repellant, octanoic, nonanoic and decanoic fatty acids (C8, 9, 10), would enhance the kill rate of a pyrethroid.

As used here, "fatty acids mixture" and a "mixture of fatty acids" refer to a mixture of octanoic, nonanoic and decanoic acids. This mixture is also referred to as "C8, 9, 10" and "C8910" herein. Octanoic, or caprylic acid, is an eight-carbon saturated fatty acid. Nonanoic acid, or pelargonic acid, is a nine-carbon saturated fatty acid. Decanoic acid, or capric acid, is a ten-carbon saturated fatty acid. The fatty acids mixture used in the mixture of the present invention is available from Emery Oleochemicals. The fatty acids mixture has an equal amount of each fatty acid by weight percentage (about 33.3% each).

In one embodiment, the invention is directed to a pesticidal mixture comprising an effective amount of a fatty acids mixture and an effective amount of a pyrethroid.

In a further embodiment, the fatty acids mixture contains about 33% of octanoic, about 33% of nonanoic, and about 33% of decanoic fatty acids.

In another embodiment, the invention is directed to a mixture wherein the pyrethroid is permethrin.

Natural pyrethrins and other pyrethroids may be used in the mixtures of the present invention. Such pyrethoids include, but are not limited to, Allethrin stereoisomers, Bifenthrin, Beta-Cyfluthrin, Cyfluthrin, Cypermethrin, d,d, trans-Cyphenothrin, Cyphenothrin, Deltamethrin, Esfenvalerate, Etofenprox Fenpropathrin, Tau-Fluvalinate, Lambda-Cyhalothrin, Gamma Cyhalothrin, Imiprothrin, 1RS cis-Permethrin, Permethrin, Prallethrin, Resmethrin, Sumithrin (d-phenothrin), Tefluthrin, Tetramethrin, Tralomethrin, and Zeta-Cypermethrin.

In a further embodiment, the invention is directed to a mixture wherein the fatty acids mixture and the pyrethroid are in a ratio from about 1000:1 to about 1:1000 by weight. The invention is also directed to a mixture wherein the fatty acids mixture and the pyrethroid are in a ratio from about 100:1 to about 1:100 by weight. In preferred embodiments, the ratio is from about 20:1 to about 1:20 by weight. In an even more preferred embodiment, the ratio is about 5:1 to about 1:5 by weight. In an even more preferred embodiment, the ratio is about 1:1 or about 1:2 by weight.

In yet another embodiment, the invention is directed to a method of insect control comprising administering to an environment in need of insect control an effective amount of the mixture disclosed above as a space spray. In an embodiment, the space spray can be an aerosol or a thermal fog spray. In one embodiment, the environment is an indoor or outdoor area where adult arthropods are present, near mosquito development sites, an outdoor area around human habitation, and indoor area of human habitation, such as a residential building, a commercial building or structure, or an agricultural crop.

In an embodiment, the mixture of the present invention may be applied by spraying or brushing the mixture onto a surface. The present invention may also be applied by residual spraying. If the mixture is used as a space spray, a ratio of fatty acids mixture to pyrethroid can be from about 1:10 to about 10:1 by weight. In a preferred embodiment, the formulation is applied at about 5:1 to about 1:5 by weight. In an even more preferred embodiment, the formulation is applied at about 1:1 or about 1:2 by weight. If the mixture is applied as a contact treatment (residual or on treated fabrics) a ratio of from about 1:100 to about 1:10,000 by weight can be used, and preferably at a ratio of about 1:100 by weight.

In a further embodiment, arthropods are controlled. Examples of arthropods that can be controlled by the mixture of the present invention include, but are not limited to insects, centipedes, millipedes and arachnids.

In another embodiment, the arthopods controlled are resistant to pyrethroids.

In a preferred embodiment, mosquitoes are controlled. In a more preferred embodiment, mosquitoes of the *Aedes aegypti* species are controlled.

In yet another embodiment, the mixture provides initial arthropod control. In another embodiment, the mixture provides residual arthropod control.

In an embodiment, the mixture may be applied to a fabric. The fabric may be a bed net, tent or an item of clothing.

Mixtures of the present invention may be formulated to produce a more storage stable or effective product. Mixtures of the present invention may be further diluted for use.

Another embodiment of the present invention is a method of using the mixture of the present invention for insect control. A preferred method of applying the formulations of the present invention is by spraying, brushing, or other means that distributes the liquid product to the environment in need of treatment. Presently, the most preferred methods of application are by space spray application or spraying or brushing an effective amount of the formulation onto a surface.

The mixture of the present invention can be applied to any environment in need of insect control. The environment in need of insect control may include any area that is desired to be free of insect infestation. For example, the formulation can be applied to an environment such as an outdoor area near mosquito development sites, an outdoor area around human habitation, an indoor area of human habitation such as a residential or commercial buildings, including single family dwellings, hotels, daycares, libraries, multi-family residences, jails, hostels, wash rooms, hallways, including hotels, and hospitals, or transportation vehicles. The environment can also be a fabric and the mixture can be applied to fabrics such as tents and clothing. The environment can also be an agricultural crop in need of protection.

The disclosed embodiments are simply exemplary embodiments of the inventive concepts disclosed herein and should not be considered as limiting, unless the claims expressly state otherwise.

As used herein, all numerical values relating to amounts, weight percentages and the like are defined as "about" or "approximately" each particular value, namely, plus or minus 10%. For example, the phrase "at least 5% by weight" is to be understood as "at least 4.5% to 5.5% by weight." Therefore, amounts within 10% of the claimed values are encompassed by the scope of the claims.

The term "effective amount" means the amount of the formulation that will kill the target insect. The "effective amount" will vary depending on the mixture concentration, the type of insect(s) being treated, the severity of the insect infestation, the result desired, and the life stage of the insects during treatment, among other factors. Thus, it is not always possible to specify an exact "effective amount." However, an appropriate "effective amount" in any individual case may be determined by one of ordinary skill in the art.

In one embodiment, the effective amount could be up to 40% of C8, 9, 10 and 40% of a pyrethroid. In a preferred embodiment, the effective amount could be from about 1% to about 40% of C8, 9, 10 and from about 1% to about 40% of the pyrethroid. This mixture may be formulated with adjuvants, such as solvents, anti-caking agents, stabilizers, defoamers, slip agents, humectants, dispersants, wetting agents, thickening agents, emulsifiers, penetrants, adjuvants, synergizers, and/or preservatives.

The following examples are intended to illustrate the present invention and to teach one of ordinary skill in the art how to use the formulations of the invention. They are not intended to be limiting in any way.

EXAMPLES

Example 1

Formulations

Preparation of octanoic, nonanoic and decanoic fatty acid (C8, 9, 10) and permethrin mixtures.

First, a 1% permethrin in acetone solution was prepared, Solution I. This solution was then used to prepare different permethrin dilutions in Solutions II and III. Butyl Hydroxy Toluene ("BHT") was used as an antioxidant. Solutions I, II, and III were then mixed with C8, 9, 10 as explained below.

TABLE 1

| Formulation ingredient | Solution I 1% Permethrin | Wt % | Order of addition |
|---|---|---|---|
| Permethrin | 1.2 | 1.0000% | 1 |
| Acetone | 118.3 | 98.6% | 2 |
| BHT | 0.5 | 0.4% | 3 |
| Total Wt | 120.00 | 100% | |

TABLE 2

| Formulation ingredient | Solution II 0.1% Permethrin | Wt % | Order of addition |
|---|---|---|---|
| Solution I | 12.5 | 10.0000% | 1 |
| Acetone | 112 | 89.6000% | 2 |
| BHT | 0.5 | 0.4000% | 3 |
| Total Wt | 125.00 | 100% | |

TABLE 3

| Formulation ingredient | Solution III 0.01% Permethrin | Wt % | Order of addition |
|---|---|---|---|
| Solution II | 20 | 10.0000% | 1 |
| Acetone | 179.2 | 89.6000% | 2 |
| BHT | 0.8 | 0.4000% | 3 |
| Total Wt | 200.00 | 100% | |

Preparation of 1% Permethrin in Acetone (Solution I; Table 1):

The above ingredients were weighed into a 250 mL bottle equipped with a magnetic stirring bar in the order of addition specified in the table above. The bottle was capped and the contents stirred using magnetic stirring until the BHT was completely dissolved.

Preparation of 0.1% Permethrin in Acetone (Solution II; Table 2):

The above ingredients were weighed into a 250 mL bottle equipped with a magnetic stirring bar in the order of addition specified in the table above. The bottle was capped and the contents stirred using magnetic stirring until the BHT was completely dissolved Preparation of 0.01% Permethrin in Acetone (Solution III; Table 3):

The above ingredients were weighed into a 250 mL bottle equipped with a magnetic stirring bar in the order of addition specified in the table above. The bottle was capped and the contents and stirred, using magnetic stirring until the BHT was completely dissolved.

Preparation of 1% C8, 9, 10+1% Permethrin in Acetone:

C8, 9, 10, 0.5 g, was weighed into a 100 mL bottle. Solution I (Table 1), 49.5 g, was then added to the bottle. The bottle was capped and the contents shaken until homogeneous.

Preparation of 1% C8, 9, 10+0.1% Permethrin in Acetone:

C8, 9, 10, 0.5 g, was weighed into a 100 mL bottle. Solution II (Table 2), 49.5 g, was then added to the bottle. The bottle was capped and the contents shaken until homogeneous.

Preparation of 1% C8, 9, 10+0.01% Permethrin in Acetone:

C8, 9, 10, 0.5 g, was weighed into a 100 mL bottle. Solution III (Table 3), 49.5 g, was then added to the bottle. The bottle was capped and the contents shaken until homogeneous.

Preparation of 1% C8, 9, 10+0.001% Permethrin in Acetone:

C8, 9, 10, 0.5 g, was weighed into a 100 mL bottle equipped with magnetic stirrer. Solution III (Table 3), 5 g, was then added to the bottle, followed by 44.3 g acetone, and 0.2 g BHT. The bottle was capped and the contents stirred magnetically until all BHT was dissolved.

Example 2

Bottle Bioassays

The following bioassays were performed to determine how pyrethroid susceptible and pyrethroid resistant *Aedes aegypti* responded to exposure to permethrin and the fatty acids mixture, separately and combined. The standard Centers for Disease Control ("CDC") bottle bioassay method was used. The testing was conducted at Centro Internacional de Entrenamiento e Investigaciones Médicas ("CIDEIM") in Colombia with susceptible and resistant *Aedes aegypti*. The compounds were diluted in acetone, added to the bottles, and bottles were rolled to coat them internally until dry. Susceptible and resistant mosquitoes were exposed inside the treated bottles.

Bottle bioassays assess susceptibility by measuring time-to-death of mosquitoes exposed in bottles coated internally with a "diagnostic concentration" of the test compound. Resistant mosquitoes will take significantly longer to be affected by contact with the material than will susceptible mosquitoes, resulting in different time/mortality curves.

Bottle Bioassay #1

In this Bioassay, pyrethroid susceptible and resistance mosquitoes were exposed to permethrin. As can be seen in FIG. 1, the pyrethroid susceptible mosquitoes had a greater mortality when exposed to permethrin than the susceptible mosquitoes. The susceptible mosquitos reach almost 100% mortality at about 80 minutes. In this study, n=5, LT ranges are 95% Cl, and error bars are standard deviation.

TABLE 4

| Strain | LT50 (min) | LT99 (min) |
|---|---|---|
| Susceptible | 18.8 | 99.3 |
| Resistant | 73.5 | 306.7 |

Bottle Bioassay #2

Figure 2:
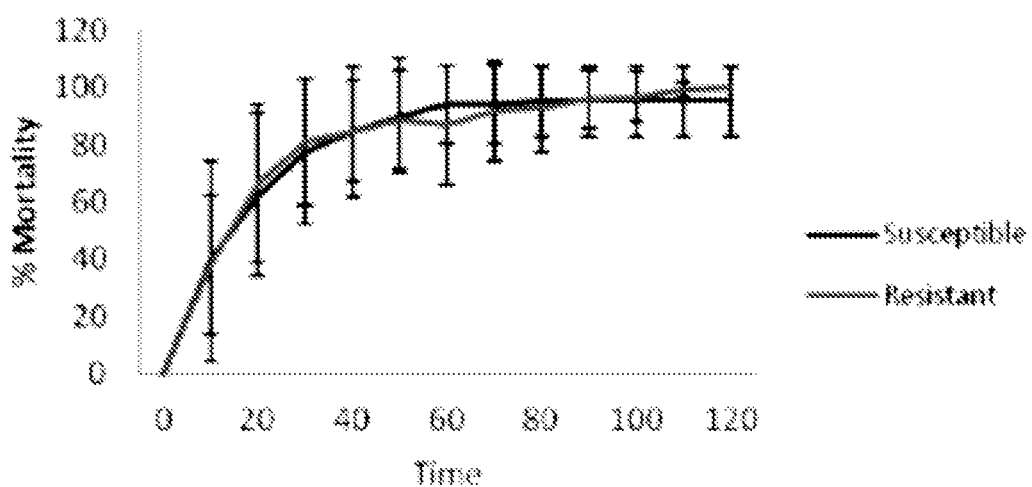
FIG. 2, Time/Mortality Response of Susceptible and Resistant *Aedes aegypti* to C8910 in Bottle Bioassay, is a graph of the results from Bottle Bioassay Example #2. This bioassay demonstrated that pyrethroid resistant and pyrethroid susceptible *Aedes aegypti* had equivalent response to a C8, 9, 10 mixture of fatty acids.

In this Bioassay, pyrethroid susceptible and resistance mosquitoes were exposed to the octanoic, nonanoic and decanoic fatty acids mixture. As can be seen in FIG. 2, the permethrin susceptible and resistant mosquitoes had equivalent responses when exposed to the octanoic, nonanoic and decanoic fatty acids mixture. Both groups showed that there were susceptible when exposed to the octanoic, nonanoic and decanoic (C8, 9, 10) fatty acids mixture. In this study, n=5, LT ranges are 95% Cl, and error bars are standard deviation.

TABLE 5

| Strain | LT50 (min) | LT99 (min) |
|---|---|---|
| Susceptible | 13.3 | 187 |
| Resistant | 13.4 | 189 |

Bottle Bioassay #3

Figure 3:
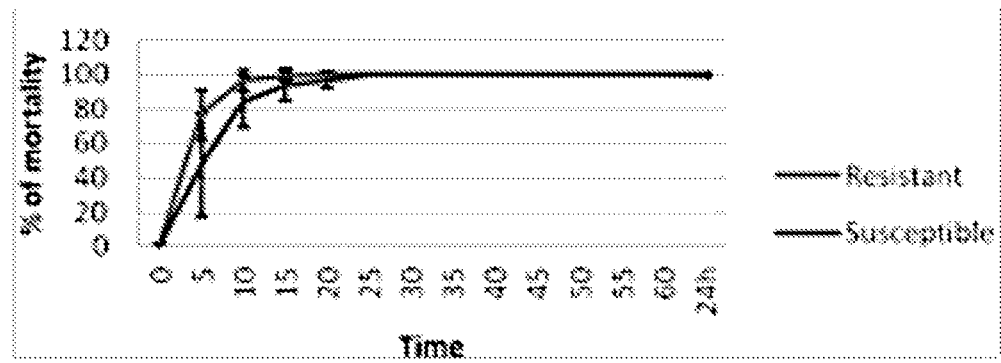
FIG. 3, Time/Mortality Response of Susceptible and Resistant *Aedes aegypti* to a 1:0.01 ratio of C8910 with Permethrin in Bottle Bioassay, is a graph of the results from Bottle Bioassay Example #3. This bioassay demonstrated that pyrethroid resistant *Aedes aegypti* had a more rapid response than did pyrethroid susceptible *Aedes aegypti* to a mixture of C8, 9, 10 fatty acids with a pyrethroid, such as permethrin.

In this Bioassay, pyrethroid susceptible and resistance mosquitoes were exposed to the combination of the octanoic, nonanoic and decanoic (C8, 9, 10) fatty acids mixture and permethrin. As can be seen in FIG. 3, the permethrin resistant mosquitoes had a more rapid response than did susceptible mosquitoes when exposed to the combination (the mortality rate of the resistant mosquitoes is represented by the line that is on top of the darker line). Both groups showed that there were susceptible when exposed to the combination. In this study, n=5, LT ranges are 95% Cl, and error bars are standard deviation.

TABLE 6

| Strain | LT50 (min) | LT99 (min) |
|---|---|---|
| Susceptible | 5.3 | 22.9 |
| Resistant | 3.2 | 13.4 |

Example 3

Topical Bioassays

The following topical bioassays were performed to determine how pyrethroid susceptible and pythroid resistant *Aedes aegypti* responded to exposure to permethrin and the fatty acids mixture, separately and combined. The standard World Health Organization ("WHO") topical bioassay method was used. The testing was conducted at CIDEIM with susceptible and resistant *Aedes aegypti*. The compounds were diluted in acetone, and 1 ul was applied to the prothorax of CO2 anesthetized mosquitoes (groups of 20—replicated 3×).

Topical bioassays focus on percent concentration delivering mortality at 24 hours, but can also assess susceptibility by measuring time-to-death of mosquitoes exposed at various concentrations. Topical assays are a closer measure of potential space spray efficacy than bottle assays, because mosquitoes receive a dose they cannot avoid (similar to spray drops).

Topical Assay #1

In this bioassay, pyrethroid susceptible and resistance mosquitoes were exposed to a 1:1 ratio of the combination of the C8, 9, 10 fatty acids mixture and permethrin. As can be seen in Table 7, the permethrin susceptible and resistant mosquitoes had equivalent responses when exposed to the combination. Both groups showed that they were susceptible when exposed to the combination at this ratio.

TABLE 7

Percent survival of resistant and susceptible *Aedes aeqypti* over time in topical assay of C8910 and Permethrin (1% and 1%)

| | Time (mins unless otherwise noted) | | | | | | |
|---|---|---|---|---|---|---|---|
| Strain | 10 | 20 | 30 | 40 | 50 | 60 | 24 hours |
| Susceptible | 36.7 | 4.2 | 5.0 | 3.5 | 3.2 | 1.5 | 1.5 |
| Resistant | 11.5 | 3.5 | 2.2 | 2.4 | 2.2 | 1.7 | 0 |

Topical Assay #2

In this bioassay, pyrethroid susceptible and resistance mosquitoes were exposed to a 10:1 ratio of the combination of the C8, 9, 10 fatty acids mixture and permethrin. As can be seen in Table 8, the permethrin susceptible and resistant mosquitoes had equivalent responses when exposed to the combination. Both groups showed that they were susceptible when exposed to the combination at this ratio.

TABLE 8

Percent survival of resistant and susceptible *Aedes aeqypti* over time in topical assay of C8910 and Permethrin (0.1% and 0.1%)

| | Time (mins unless otherwise noted) | | | | | | |
|---|---|---|---|---|---|---|---|
| Strain | 10 | 20 | 30 | 40 | 50 | 60 | 24 hours |
| Susceptible | 27.7 | 36.8 | 6.8 | 5.7 | 3.7 | 3.7 | 0 |
| Resistant | 24.8 | 20.6 | 7.0 | 4.4 | 1.9 | 1.44 | 0 |

Topical Assay #3

In this bioassay, pyrethroid susceptible and resistance mosquitoes were exposed to a 1:1 ratio of the combination of the C8, 9, 10 fatty acids mixture and permethrin at a 0.1% concentration. As can be seen in Table 9, the permethrin susceptible and resistant mosquitoes had equivalent responses when exposed to the combination. Both groups showed that they were susceptible when exposed to the combination at this ratio.

TABLE 9

Percent survival of resistant and susceptible *Aedes aeqypti* over time in topical assay of C8910 and Permethrin (1% and 1%)

| | Time (mins unless otherwise noted) | | | | | | |
|---|---|---|---|---|---|---|---|
| Strain | 10 | 20 | 30 | 40 | 50 | 60 | 24 hours |
| Susceptible | 12.3 | 26.4 | 27.1 | 25.0 | 22.5 | 20.4 | 5.9 |
| Resistant | 29.6 | 31.2 | 27.0 | 18.6 | 14.3 | 12.4 | 0 |

Example 4

Wind Tunnel Assays

In this bioassay, the standard WHO wind tunnel bioassay was used by CIDEIM. *Aedes aegypti* that were known to be resistant and susceptible to permethrin were used in the studies. Four solutions were prepared with the following ratios of C8, 9, 10 fatty acids mixture to permethrin: 2:1 (0.67% C8910+0.33% permethrin); 1:1 (0.5% C8910+0.5% permethrin); and 1:2 (0.33% C8910+0.67% permethrin). A one percent permethrin formulation was tested as well as a C8, 9, 10 fatty acids mixture.

The solutions were diluted in acetone to 1%, 0.1%, 0.01%, 0.001%, 0.0001%, and 0.00001%. Then 0.5 ml of each dilution was sprayed into the wind tunnel. This exposed 20 caged mosquitos to the spray. Each test was replicated three times. The 24 hour mortality was then observed. This type of assay is desirable because it tests the compounds without being formulated.

The results of this study indicated that 1:1, 1:2 and 2:1 ratios of the combination of the C8, 9, 10 fatty acids mixture and permethrin were effective at killing susceptible and resistant mosquitos. The C8, 9, 10 fatty acids mixtures alone did not provide significant mortality by themself in any of the assays.

As expected, resistant mosquitos showed lower mortality rates than susceptible mosquitos when exposed to permethrin. However, unexpectedly, a high number of permethrin resistant mosquitos were killed by the combination of C8, 9, 10 fatty acids and permethrin.

This study shows that there was a synergistic effect between C8, 9, 10 fatty acids mixture and permethrin because the results were more than additive. Further, the combination of C8, 9, 10 fatty acids mixture with permethrin achieved the same kill rate as permethrin when 33% to 50% less permethrin was used.

Example 5

Wind Tunnel Assay

In this bioassay, *Aedes aegypti* known to be resistant to permethrin (Key West strain) were exposed to C8, 9, 10 alone, permethrin alone, and combinations of C8, 9, 10 and permethrin at 1:5, 1:2, 1:1, 2:1 and 5:1 ratios in a standard wind tunnel bioassay. The actives were suspended in 1 milliliter oil-based ultra-low volume sprays and sprayed into the wind tunnel. This exposed 80 caged *A. aegypti* to the spray. Each test was replicated four times. Fifteen-minute, one-hour and twenty-four hour mortality of the resistant *A. aegypti* was then observed. Results are below in Table 10.

Synergy was calculated using Abbott's synergy equation described in Levy Y et al., The joint action of fungicides in mixtures: comparison of two methods for synergy calculation, *Bulletin OEPP/EPPO Bulletin*,1986, 16, 651-657. Specifically, a ratio greater than 1.0 of observed to expected percent mortality for combinations of two pesticides is evidence of synergy. Expected % mortality was calculated using the formula % Cexp=A+B−(AB) where A is percent mortality of *A. aegypti* exposed to C8, 9, 10, B is percent mortality of *A. aegypti* exposed to permethrin and Cexp is expected percent mortality of *A. aegypti* exposed to a combination of C8, 9, 10 and permethrin.

TABLE 10

Percent survival of resistant and susceptible *Aedes aegypti* over time in wind tunnel assay of C8910 and Permethrin

|  | % A.I. | | Ratio | % Mortality | | |
|---|---|---|---|---|---|---|
|  | C 8, 9, 10 | Permethrin | C:P | 15 min | 1 hour | 24 hour |
| Observed | 0.8% | 0% | n/a | 0.0% | 0.9% | 1.6% |
|  | 2.0% | 0% | n/a | 0.3% | 1.6% | 5.3% |
|  | 4.0% | 0% | n/a | 0.0% | 9.1% | 16.6% |
|  | 8.0% | 0% | n/a | 0.0% | 1.2% | 13.1% |
|  | 0% | 1.6% | n/a | 28.1% | 41.6% | 55.0% |
|  | 0% | 4.0% | n/a | 34.4% | 49.4% | 63.4% |
|  | 4.0% | 4.0% | 1:1 | 51.9% | 80.6% | 90.0% |
|  | 8.0% | 1.6% | 5:1 | 40.6% | 60.9% | 70.0% |
|  | 0.8% | 4.0% | 1:5 | 32.2% | 62.5% | 74.4% |
|  | 8.0% | 4.0% | 2:1 | 54.4% | 67.2% | 74.4% |
|  | 2.0% | 4.0% | 1:2 | 60.9% | 70.0% | 89.7% |
| Expected | 4.0% | 4.0% | 1:1 | 34.4% | 54.0% | 69.5% |
|  | 8.0% | 1.6% | 5:1 | 28.1% | 42.3% | 60.9% |
|  | 0.8% | 4.0% | 1:5 | 34.4% | 49.9% | 64.0% |
|  | 8.0% | 4.0% | 2:1 | 34.4% | 50.0% | 68.2% |
|  | 2.0% | 4.0% | 1:2 | 34.6% | 50.2% | 65.4% |
| Synergy Ratio | 4.0% | 4.0% | 1:1 | 1.5 | 1.5 | 1.3 |
|  | 8.0% | 1.6% | 5:1 | 1.4 | 1.4 | 1.1 |
|  | 0.8% | 4.0% | 1:5 | 0.9 | 1.3 | 1.2 |
|  | 8.0% | 4.0% | 2:1 | 1.6 | 1.3 | 1.1 |
|  | 2.0% | 4.0% | 1:2 | 1.8 | 1.4 | 1.4 |

As seen in Table 10, combinations of C8, 9, 10 and permethrin were synergistic at all five ratios (i.e. 1:5, 1:2, 1:1, 2:1 and 5:1) at one-hour and twenty-four hours post-application and for four of the five ratios at fifteen-minutes post application.

Example 6

Wind Tunnel Assay

In this assay, *A. aegypti* known to be susceptible to permethrin (Benzon research strain) were exposed to C8, 9, 10 alone, permethrin alone, and combinations of C8, 9, 10 and permethrin at 1:5, 1:2, 1:1, 2:1 and 5:1 ratios in a standard wind tunnel bioassay identical to that described above. Results are below in Table 11.

TABLE 11

Percent survival of resistant and susceptible *Aedes aegypti* over time in wind tunnel assay of C8910 and Permethrin

|  | % A.I. | | Ratio | % Mortality | | |
|---|---|---|---|---|---|---|
|  | C 8, 9, 10 | Permethrin | C:P | 15 min | 1 hour | 24 hour |
| Observed | 0.2% | 0% | n/a | 0.0% | 4.1% | 13.1% |
|  | 0.5% | 0% | n/a | 8.1% | 31.9% | 39.1% |
|  | 1.0% | 0% | n/a | 0.0% | 0.62% | 5.31% |
|  | 2.0% | 0% | n/a | 0.0% | 0.31% | 11.0% |
|  | 0% | 0.4% | n/a | 4.4% | 34.1% | 42.5% |
|  | 0% | 1.0% | n/a | 26.9% | 54.4% | 65.3% |
|  | 1.0% | 1.0% | 1:1 | 48.1% | 70.3% | 74.4% |
|  | 2.0% | 0.4% | 5:1 | 37.2% | 67.5% | 70.6% |
|  | 0.2% | 1.0% | 1:5 | 33.4% | 55.3% | 62.8% |
|  | 2.0% | 1.0% | 2:1 | 47.8% | 61.6% | 68.1% |
|  | 0.5% | 1.0% | 1:2 | 51.6% | 69.7% | 74.4% |
| Expected | 1.0% | 1.0% | 1:1 | 26.9% | 54.7% | 67.2% |
|  | 2.0% | 0.4% | 5:1 | 4.4% | 34.3% | 48.8% |
|  | 0.2% | 1.0% | 1:5 | 26.9% | 56.2% | 69.9% |
|  | 2.0% | 1.0% | 2:1 | 26.9% | 54.5% | 69.1% |
|  | 0.5% | 1.0% | 1:2 | 32.8% | 68.9% | 78.9% |
| Synergy Ratio | 1.0% | 1.0% | 1:1 | 1.8 | 1.3 | 1.1 |
|  | 2.0% | 0.4% | 5:1 | 8.5 | 2.0 | 1.4 |
|  | 0.2% | 1.0% | 1:5 | 1.2 | 1.0 | 0.9 |
|  | 2.0% | 1.0% | 2:1 | 1.8 | 1.1 | 1.0 |
|  | 0.5% | 1.0% | 1:2 | 1.6 | 1.0 | 0.9 |

As seen in Table 11, combinations of C8, 9, 10 and permethrin were synergistic at all five ratios (i.e. 1:5, 1:2, 1:1, 2:1 and 5:1) at fifteen-minutes post application and for three of the five ratios at one-hour and two of the five at twenty-four hours post application.

The invention claimed is:

1. A pesticidal mixture comprising an effective amount of a mixture of octanoic, nonanoic and decanoic (C8, 9, 10) fatty acids and an effective amount of a pyrethroid, wherein the mixture of octanoic, nonanoic and decanoic (C8, 9, 10) fatty acids and the pyrethroid are in a ratio from about 5:1 to about 1:5 by weight.

2. A method of insect control comprising administering to an environment in need of insect control an effective amount of the mixture of claim 1.

3. The method of claim 2 wherein the environment is an outdoor area in need of insecticidal treatments.

4. The method of claim 2 wherein the environment is an agricultural crop.

5. The method of claim 2 wherein the environment is a residential or commercial building or structure.

6. The method of claim 2 wherein the mixture is applied by spraying or brushing the mixture onto a surface.

7. The method of claim 2 wherein arthropods are controlled.

8. The method of claim 7 wherein the arthropods are mosquitoes.

9. The method of claim 2 wherein the mixture provides residual insect control.

10. The method of claim 2 wherein the mixture provides immediate kill of flying insects when applied as a space spray.

11. A method of insect control comprising applying an effective amount of the mixture of claim 1 to a fabric.

12. The method of claim 11 wherein the fabric is a bed net, a tent or an item of clothing.

13. The method of claim 11 wherein the insects controlled are mosquitoes.

14. The method of claim 13 wherein the mosquitoes are *Aedes aegypti* species.

15. The method of claim 13 wherein the mosquitoes are pyrethroid-resistant.

* * * * *